United States Patent
Anzai (10) Patent No.: US 11,439,733 B2
(45) Date of Patent: Sep. 13, 2022

(54) METHOD FOR PRODUCING ANTITHROMBOTIC COATING MATERIAL

(71) Applicant: TERUMO KABUSHIKI KAISHA, Tokyo (JP)

(72) Inventor: Takao Anzai, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 414 days.

(21) Appl. No.: 16/207,546

(22) Filed: Dec. 3, 2018

(65) Prior Publication Data

US 2019/0099525 A1    Apr. 4, 2019

Related U.S. Application Data

(62) Division of application No. 15/066,564, filed on Mar. 10, 2016, now Pat. No. 10,188,774.

(30) Foreign Application Priority Data

| Mar. 10, 2015 | (JP) | 2015-047610 |
| Jul. 29, 2015 | (JP) | 2015-150087 |
| Jan. 5, 2016 | (JP) | 2016-000592 |

(51) Int. Cl.
| A61L 33/06 | (2006.01) |
| A61L 27/54 | (2006.01) |
| A61L 29/08 | (2006.01) |
| A61L 31/10 | (2006.01) |
| C08L 33/06 | (2006.01) |

(52) U.S. Cl.
CPC .............. *A61L 33/064* (2013.01); *A61L 27/54* (2013.01); *A61L 29/085* (2013.01); *A61L 31/10* (2013.01)

(58) Field of Classification Search
CPC ........ C08L 33/06; A61L 27/54; A61L 29/085; A61L 31/10; A61L 33/064; A61L 33/06
See application file for complete search history.

(56) References Cited

U.S. PATENT DOCUMENTS

| 6,590,054 | B2 * | 7/2003 | Tanaka | A61L 33/064 526/259 |
| 2004/0171765 | A1 | 9/2004 | Tsuji et al. | |
| 2008/0274074 | A1 | 11/2008 | Couturier et al. | |
| 2009/0234090 | A1 * | 9/2009 | Ogawa | C09D 133/26 526/304 |
| 2014/0235748 | A1 * | 8/2014 | Haraguchi | A61L 33/064 523/112 |

FOREIGN PATENT DOCUMENTS

JP    04-152952 A    5/1992

* cited by examiner

*Primary Examiner* — Anna R Falkowitz
(74) *Attorney, Agent, or Firm* — Buchanan Ingersoll & Rooney PC (57) ABSTRACT

Provided is a method for producing an antithrombotic coating material in which a high molecular weight polymer can be obtained by a solution polymerization using a radical polymerization initiator. The above-mentioned task is achieved by a method for producing an antithrombotic coating material, including steps of: preparing a methanol solution containing a monomer represented by formula (1):

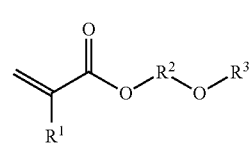

(1)

wherein in formula (1), $R^1$, $R^2$, and $R^3$ are the same as those described in the specification, respectively; adding a radical polymerization initiator having a 10-hour half-life temperature of 60° C. or less to the methanol solution to prepare a polymerization reaction liquid; and polymerizing the monomer.

10 Claims, 3 Drawing Sheets

METHOD FOR PRODUCING ANTITHROMBOTIC COATING MATERIAL

CROSS-REFERENCES TO RELATED APPLICATIONS

This application is a divisional of U.S. application Ser. No. 15/066,564 filed Mar. 10, 2016, which claims the benefit of priority of Japanese Application No. 2015-047610 filed on Mar. 10, 2015, Japanese Application No. 2015-150087 filed on Jul. 29, 2015, and Japanese Application No. 2016-000592 filed on Jan. 5, 2016, the entire content of which is incorporated herein by reference.

TECHNICAL FIELD

The present disclosure relates to a method for producing an antithrombotic coating material.

BACKGROUND DISCUSSION

Recently, studies on medical materials utilizing various polymer materials have been in progress, and their application to membranes for artificial kidney, membranes for blood plasma separation, catheters, stents, membranes for artificial lung, artificial blood vessels, anti-adhesion barriers, artificial skin, and the like, is possible. For such applications, synthetic polymer materials, which are foreign matters in the living body, are used in contact with biological tissue, or body fluid such as blood. Accordingly, it can be desirable for the medical materials to have biocompatibility. The desired biocompatibility of the medical materials varies depending on their purpose or usage, but it can be desirable for medical materials used as materials in contact with blood to have antithrombotic properties such as, for example, inhibition of the blood coagulation system, suppression of adhesion and activation of platelets, and inhibition of activation of the complement system.

In general, impartment of the antithrombotic property to a medical equipment is carried out by a method of coating a substrate constituting the medical equipment with an antithrombotic material (antithrombotic coating material), or a method of fixing an antithrombotic material to the surface of the substrate.

For example, JP-A-4-152952 discloses a membrane for artificial organs and a medical equipment for use in contact with biological tissue or blood, which have, on their surfaces, a synthetic polymer that satisfies effects of suppression of adhesion and activation of platelets, and inhibition of activation of the complement system, as well as biocompatibility which is affinity with the biological tissue. In JP-A-4-152952, polymethoxyethyl acrylate (PMEA) or the like is disclosed as a synthetic polymer that is an antithrombotic material.

SUMMARY

Polymethoxyethyl acrylate (PMEA) is a hydrophilic polymer material that is excellent in antithrombotic property and biocompatibility, and employed as an antithrombotic component of a surface coating material of a medical equipment in contact with blood. PMEA is hydrophilic, and thus, when used for the antithrombotic coating material, one having a higher molecular weight can be desirable because the stability of the coat layer increases.

As a polymerization method of PMEA, a solution polymerization using a radical polymerization initiator can be used. The solution polymerization is advantageous in that catalysts do not remain and that it can be implemented at a low cost, but conventionally, a polymer having a high molecular weight was hardly obtained by the solution polymerization using a radical polymerization initiator.

The present disclosure has been made, for example, in view of the above circumstances. According to an exemplary aspect, provided is a method for producing an antithrombotic coating material in which a high molecular weight polymer can be obtained by a solution polymerization using a radical polymerization initiator.

The present inventors have conducted extensive research, for example, to address the problems mentioned above. As a result, for example, disclosed is a method for producing an antithrombotic coating material, including steps of preparing a methanol solution containing a monomer such as methoxyethyl acrylate, adding a radical polymerization initiator having a 10-hour half-life temperature of 60° C. or less to the methanol solution, and polymerizing the monomer.

According to the present disclosure, for example, there is provided a method for producing an antithrombotic coating material in which a high molecular weight polymer can be obtained by a solution polymerization using a radical polymerization initiator.

DETAILED DESCRIPTION

According to an exemplary aspect, the present disclosure relates to a method for producing an antithrombotic coating material, including steps of preparing a methanol solution containing a monomer such as methoxyethyl acrylate, adding a radical polymerization initiator having a 10-hour half-life temperature of 60° C. or less to the methanol solution to prepare a polymerization reaction liquid and polymerizing the monomer. The production method according to the disclosure can increase the molecular weight of the obtained polymer while employing the solution polymerization using a radical polymerization initiator. When the molecular weight of the polymer contained in the antithrombotic coating material is high, the stability of the coat layer is enhanced. While not intended to limit the technical scope of the present disclosure, it is considered that the higher the molecular weight of polymers, the more easily polymers become entangled with each other, so that the coat layer formed on a substrate is stabilized.

Hereinafter, exemplary embodiments of the disclosure will be described. The present disclosure is not limited to the following embodiments.

Further, in the present specification, the expression "X to Y", which represents a range, means "X or more and Y or less". Unless otherwise particularly specified, operations and measurements of properties are carried out under conditions of room temperature (20 to 25° C.) and a relative humidity of 40 to 50%.

An exemplary production method according to the disclosure includes a step of preparing a methanol solution containing a monomer represented by formula (1) below (methanol solution preparing step).

(1)

In formula (1), $R^1$ is a hydrogen atom or a methyl group, for example, a hydrogen atom.

In formula (1), $R^2$ is a cyclic, straight, or branched alkylene group having 1 to 4 carbon atoms, for example, a straight or branched alkylene group having 1 to 4 carbon atoms. Specific examples thereof include a methylene group, an ethylene group, a trimethylene group, a propylene group, a cyclopropylene group, a tetramethylene group, and a cyclobutylene group. Among them, in consideration of the effect of enhancing the antithrombotic property, $R^2$ can be a straight or branched alkylene group having 1 to 3 carbon atoms, for example, a methylene group or an ethylene group.

In formula (1), $R^3$ is a cyclic, straight, or branched alkyl group having 1 to 4 carbon atoms, for example, a straight or branched alkyl group having 1 to 4 carbon atoms. Specific examples thereof include a methyl group, an ethyl group, a propyl group, an isopropyl group, a n-butyl group, a sec-butyl group, a tert-butyl group, and a cyclopropyl group. Among them, in consideration of the effect of enhancing the antithrombotic property, $R^3$ can be a straight or branched alkyl group having 1 to 3 carbon atoms, for example, a methyl group or an ethyl group, for example, a methyl group. Specific examples of the monomer represented by formula (1) include methoxymethyl acrylate, methoxyethyl acrylate (MEA), methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate. The monomer represented by formula (1) can be methoxymethyl acrylate, methoxyethyl acrylate (MEA), ethoxymethyl acrylate, ethoxyethyl acrylate, methoxymethyl methacrylate, methoxyethyl methacrylate, ethoxymethyl methacrylate, or ethoxyethyl methacrylate, and in terms of ease of availability, for example, methoxyethyl (meth)acrylate. These monomers may be used either alone or in mixture of two or more thereof.

In the present disclosure, "(meth)acrylate" means "acrylate" and/or "methacrylate."

In the method according to the disclosure, in addition to the monomer represented by formula (1), other monomers that are copolymerizable with the monomer represented by formula (1) (hereinafter, also referred to as "other monomers") may be used. Examples of the other monomers that are copolymerizable with the monomer represented by formula (1) include acrylamide, N,N-dimethylacrylamide, N,N-diethylacrylamide, aminomethylacrylate, aminoethylacrylate, aminoisopropylacrylate, diaminomethylacrylate, diaminoethylacrylate, diaminobutylacrylate, methacrylamide, N,N-dimethylmethacrylamide, N,N-diethylmethacrylamide, aminomethylmethacrylate, aminoethylmethacrylate, diaminomethylmethacrylate, diaminoethylmethacrylate, methylacrylate, ethylacrylate, isopropylacrylate, butylacrylate, 2-ethylhexylacrylate, methylmethacrylate, ethylmethacrylate, butylmethacrylate, hexylacrylate, hexylmethacrylate, ethylene, and propylene.

When the other monomers are used in the methanol solution preparing step, the ratio of the other monomers is, for example, 10 to 50 wt %, for example, 15 to 30 wt % based on the total monomers.

In an embodiment of the present disclosure, the monomer used in the methanol solution preparing step is the monomer represented by formula (1).

In the present disclosure, methanol is used as a main component of a polymerization solvent. If a solvent other than methanol is used as the main component of the polymerization solvent, for example, it is difficult to increase the molecular weight of the polymer. While not intended to limit the technical scope of the present disclosure, it is considered that this is due to mobility of growing radicals during the polymerization.

For example, the "methanol solution" in an exemplary embodiment can contain methanol as the main component of the polymerization solvent, and a solvent other than methanol can be further included therein, within a range where a desired effect of the present disclosure is not impaired. The expression "as the main component" means that methanol accounts for 95 wt % or more, for example, 99 wt % or more (upper limit: 100 wt %) in the whole solvent used in the methanol solution. The polymerization solvent other than methanol, which is contained in the "methanol solution", may include one or more selected from, for example, water; alcohols such as ethanol, isopropanol, n-propanol, n-butanol, isobutanol, sec-butanol, tert-butanol, ethylene glycol, diethylene glycol, propylene glycol, and dipropylene glycol; and organic solvents such as chloroform, tetrahydrofuran, acetone, dioxane, and benzene, but not limited thereto. When a solvent other than methanol is contained in the "methanol solution", the content of the solvent other than methanol (in a case where two or more kinds are contained, the total thereof) is, for example 5 parts by weight or less, for example, 1 part by weight or less based on 100 parts by weight of methanol.

In an exemplary embodiment, the polymerization solvent contained in the "methanol solution" is composed of methanol only. The content of the monomer represented by formula (1) that is contained in the methanol solution can be 10 wt % or more, for example, 20 wt % or more, for example, 25 wt % or more, for example, 30 wt % or more based on the whole methanol solution, in terms of the magnitude of the resulting molecular weight. Since the molecular weight of the resulting polymer increases as the content of the monomer in the methanol solution increases, the upper limit of the content of the monomer represented by formula (1) in the methanol solution can be, for example, a saturated concentration or less, for example, 70 wt % or less, for example, 60 wt % or less. Further, when other monomers are contained in the methanol solution, the whole monomer content (the total of the monomer represented by formula (1) and the other monomers) in the methanol solution is, for example, a saturated concentration or less. At the time of preparing the methanol solution, stirring may be carried out as desired.

In the methanol solution preparing step, the methanol solution, to which the monomers have been added, may be subjected to a degassing treatment prior to addition of a polymerization initiator. In the degassing treatment, the methanol solution may be bubbled with an inert gas such as, for example, nitrogen gas or argon gas for 0.5 to 5 hours. At the time of the degassing treatment, the temperature of the methanol solution may be adjusted to about 30° C. to 80° C., for example, a polymerization temperature in the subsequent polymerization step.

The method according to the disclosure includes a step of preparing a polymerization reaction liquid prepared by adding a radical polymerization initiator having a 10-hour half-life temperature of 60° C. or less to the methanol solution (the "polymerization reaction liquid prepared by adding a radical polymerization initiator having a 10-hour half-life temperature of 60° C. or less to the methanol solution" is also referred to as a "polymerization reaction liquid"), and polymerizing the monomer (polymerization step).

In the polymerization step, a radical polymerization initiator having a 10-hour half-life temperature of 60° C. or less is used. When a radical polymerization initiator having a 10-hour half-life temperature exceeding 60° C., such as 2,2'-azobisisobutyronitrile (AIBN, T10=65° C.) or dimethyl 2,2'-azobis(2-methylpropionate)(T10=66° C.), is used, it is necessary to carry out the polymerization at a high temperature exceeding 60° C. Therefore, when the monomer concentration is low, a chain transfer reaction to the solvent, monomers, and polymers easily occurs in the radical polymerization, and thus, it is difficult to obtain a polymer having a high molecular weight. In addition, when the monomer concentration is high, since the polymerization is carried out at a high temperature, the polymerization rate is increased. In addition, since the growing radicals are hardly diffused, the polymer itself is gelled and insolubilized.

In the present disclosure, the "10-hour half-life temperature (T10)" means a temperature necessary for a concentration to decrease to half of the initial value (e.g., 0.01 mol/L) in 10 hours in a radically inert solvent such as benzene.

Examples of the radical polymerization initiator having a 10-hour half-life temperature of 60° C. or less include, but are not particularly limited to, 2,2'-azobis(4-methoxy-2,4-dimethylvaleronitrile) (T10=30° C.), 2,2'-azobis(2,4-dimethylvaleronitrile) (T10=51° C.), 2,2'-azobis[2-(2-imidazolin-2-yl)propane] dihydrochloride (T10=44° C.), 2,2'-azobis[2-(2-imidazolin-2-yl)propane] disulfate dihydrate (T10=46° C.), 2,2'-azobis(2-methylpropionamidine) dihydrochloride (T10=56° C.), 2,2'-azobis[N-(2-carboxyethyl)-2-methylpropionamidine)] hydrate (T10=57° C.), 3-hydroxy-1,1-dimethylbutyl peroxyneodecanoate (T10=37° C.), α-cumyl peroxyneodecanoate (T10=38° C.), 1,1,3,3-tetrabutyl peroxyneodecanoate (T10=44° C.), t-butyl peroxyneodecanoate (T10=48° C.), t-butyl peroxyneoheptanoate (T10=53° C.), t-butyl peroxypivalate (T10=58° C.), t-amyl peroxyneodecanoate (T10=46° C.), t-amyl peroxypivalate (T10=55° C.), di(2-ethylhexyl) peroxydicarbonate (T10=49° C.), and di(secondary-butyl) peroxydicarbonate (T10=51° C.). Among them, exemplary is a radical polymerization initiator having a 10-hour half-life temperature of 50° C. or less, and exemplary is 2,2'-azobis(4-methoxy-2,4-dimethylvaleronitrile), 3-hydroxy-1,1-dimethylbutylperoxyneodecanoate, or α-cumyl peroxyneodecanoate, which has a very low 10-hour half-life temperature of 40° C. or less. These radical polymerization initiators may be commercially available, and examples thereof include V-70 (T10=30° C.), V-65 (T10=51° C.), VA-044 (T10=44° C.), VA-046B (T10=46° C.), VA-50 (T10=56° C.), and VA-057 (T10=57° C.) (all manufactured by Wako Pure Chemical Industries, Ltd.), AZO Series ADVN (T10=52° C.) (manufactured by Otsuka Chemical Co., Ltd.), and Luperox™ 610 (T10=37° C.), Luperox™ 188 (T10=38° C.), Luperox™ 844 (T10=44° C.), Luperox™ 10 (T10=48° C.), Luperox™ 701 (T10=53° C.), Luperox™ 11 (T10=58° C.), Luperox™ 546 (T10=46° C.), Luperox™ 554 (T10=55° C.), Luperox™ 223 (T10=49° C.), and Luperox™ 225 (T10=51° C.) (all manufactured by Arkema Yoshitomi, Ltd.).

The amount of the radical polymerization initiator having a 10-hour half-life temperature of 60° C. or less is, for example, 0.005 to 2 parts by weight, for example, 0.1 to 0.5 parts by weight based on 100 parts by weight of the monomer (in a case where two or more monomers are used, the total thereof). For example, when the amount of the radical polymerization initiator having a 10-hour half-life temperature of 60° C. or less is 0.005 parts by weight or more based on 100 parts by weight of the monomer, there is an advantage that a desired high molecular weight matter is obtained with a good reproducibility. For example, when the amount is 2 parts by weight or less, there is an advantage that reduction in molecular weight is prevented.

The radical polymerization initiator may be added to methanol in any concentration, and followed by addition to the methanol solution containing the monomer as an initiator methanol liquid. The content of the radical polymerization initiator in the initiator methanol liquid is, for example, 0.01 to 10 wt %.

In the initiator methanol liquid, a solvent other than methanol can be included therein, for example, within a range where a desired effect of the present disclosure is not impaired. For example, the initiator methanol liquid may contain, for example, 5 parts by weight or less (e.g., 1 part by weight or less) of the solvent other than methanol based on 100 parts by weight of methanol.

As for the content of the monomer represented by formula (1) contained in the polymerization reaction liquid in the polymerization step, the content of the monomer contained in the polymerization reaction liquid is, for example, 10 wt % or more based on the whole polymerization reaction liquid, in terms of the magnitude of the resulting molecular weight. The content of the monomer contained in the polymerization reaction liquid is, for example, 20 wt % or more, for example, 25 wt % or more, for example, 30 wt % or more based on the whole polymerization reaction liquid. Since the molecular weight of the resulting polymer increases as the content of the monomer in the polymerization reaction liquid increases, the upper limit of the content of the monomer represented by formula (1) in the polymerization reaction liquid is, but not particularly limited to, for example, a saturated concentration or less, for example, 70 wt % or less, for example, 60 wt % or less. In an embodiment of the present disclosure, the content of the monomer represented by formula (1) contained in the polymerization reaction liquid is from 20 wt % to a saturated concentration. Further, when the polymerization reaction liquid contains other monomers, the whole monomer content (the total of the monomer represented by formula (1) and the other monomers) in the polymerization reaction liquid is, for example, a saturated concentration or less. At the time of preparing the polymerization reaction liquid, stirring may be carried out as necessary.

In terms of increase in molecular weight of the polymer and prevention of gelation in the polymerization step, the polymerization temperature is, for example, a low temperature, but if excessively low, the progress of the reaction becomes slow, thereby lowering the production efficiency. The polymerization temperature is, for example, 30 to 60° C., for example, 40 to 55° C.

The polymerization time is, for example, 1 to 24 hours, for example, 3 to 12 hours at the above-mentioned polymerization temperature.

Furthermore, if desired, a polymerization rate regulator, a surfactant, and other additives may be used during the polymerization as appropriate.

The atmosphere in which the polymerization reaction is performed is not particularly limited, but the polymerization reaction may be performed under an air atmosphere, or an inert gas atmosphere such as nitrogen gas or argon gas. Further, the reaction liquid may be stirred during the polymerization reaction.

The polymerized polymer may be purified by a general purification such as re-precipitation, dialysis, ultrafiltration, or extraction.

The purified polymer may be dried by any method such as freeze drying, vacuum drying, spray drying, or heat drying, but in terms of reducing the impact on the properties of the polymer, freeze drying or vacuum drying is exemplary.

According to the solution polymerization using the radical polymerization initiator, it is possible to obtain a polymer having a high molecular weight. The weight average molecular weight of the polymer obtained by the polymerization of the monomer is, for example, 200,000 or more, for example, more than 300,000, for example, 400,000 or more, in terms of the stability of the coat layer. The upper limit of the molecular weight of the polymer is, but not particularly limited to, for example, 1,000,000 or less, for example, less than 1,000,000, for example, 800,000 or less in terms of the fact that the polymer itself, for example, is not gelled and insolubilized.

In an exemplary embodiment, the weight average molecular weight of the polymer obtained by the polymerization of the monomer is more than 300,000 and 1,000,000 or less.

The "weight average molecular weight" as used in the present disclosure can be calculated by gel permeation chromatography (GPC) in terms of polystyrene as a standard material. Specifically, the polymer is dissolved in tetrahydrofuran (THF) to be 1 mg/ml. The GPCs of the standard polystyrene and the polymer are measured by using a GPC system LC-20 (manufactured by Shimadzu Corporation) equipped with a Shodex GPC column LF-804 (manufactured by Showa Denko K.K.) and pouring THF as a moving phase. A calibration curve is plotted with the standard polystyrene to thereby calculate the weight average molecular weight of the polymer.

The antithrombotic coating material obtained by the production method according to the disclosure may include the polymer obtained by the above-mentioned steps. The production method according to the disclosure may further include a step of adding other additives such as a gelling agent, a thickener, a plasticizer, or a solvent to the polymer which is then processed into a form such as a gel form or a solution form. Optionally, the production method may include a step of adding other components such as a crosslinking agent, a thickener, a preservative, or a pH adjustor to the polymer to obtain a composition. When the antithrombotic coating material contains a crosslinking agent, the polymer may be immobilized more firmly to a substrate surface.

When used in a form of a composition, a medium to be used is not particularly limited; for example, the polymer can be dissolved, suspended, or dispersed therein, and examples thereof may include water, toluene, xylene, diethyl ether, chloroform, ethyl acetate, methylene chloride, tetrahydrofuran, acetone, acetonitrile, N,N-dimethylformamide, dimethyl sulfoxide, methanol, ethanol, propanol, n-butanol, ethylene glycol, diethylene glycol, propylene glycol, and dipropylene glycol. The medium may be used either alone or in mixture of two or more thereof. Among them, in terms of the solubility of the polymer, the solvent to be used is, for example, methanol.

The amount of the polymer contained in the composition may be arbitrarily set, or a solution obtained by dissolving the polymer to a saturation amount may be used. The amount of the polymer may be, for example, 0.1 to 50 wt % based on the whole coating material.

An unreacted monomer contained in the antithrombotic coating material is, for example, 0.01 wt % or less based on the whole polymer. The lower limit is not particularly limited because it is exemplary that the amount of the unreacted monomer is, for example, as small as possible and may be, for example, 0 wt %. The content of the residual monomer may be measured by a method known to those skilled in the art, such as, for example, a high performance liquid chromatography.

In an exemplary embodiment of the present disclosure, there is provided an antithrombotic coating material including polyalkoxyalkyl (meth)acrylate that contains a structural unit (A) represented by formula (2) below, has a weight average molecular weight of 200,000 or more (hereinafter, the "polyalkoxyalkyl (meth)acrylate that contains the structural unit (A) represented by formula (2) below and has the weight average molecular weight of 200,000 or more" is also referred to as a "polymer according to the disclosure"), and is dissolved in methanol or a mixture of water and methanol. An exemplary embodiment relates to a composition for imparting an antithrombotic property, containing polyalkoxyalkyl (meth)acrylate that contains a structural unit (A) represented by formula (2) below and has a weight average molecular weight of 200,000 or more, and methanol or a mixture of water and methanol. When the polyalkoxyalkyl (meth)acrylate contained in the coat layer has a high molecular weight, for example, the stability of the coat layer becomes excellent as described above.

In formula (2), $R^1$ represents a hydrogen atom or a methyl group, $R^2$ represents an alkylene group having 1 to 4 carbon atoms, and $R^3$ represents an alkyl group having 1 to 4 carbon atoms. For $R^1$, $R^2$, and $R^3$ in formula (2), the descriptions for $R^1$, $R^2$, and $R^3$ described above for formula (1) are applied, respectively.

The antithrombotic coating material containing the hydrophilic material having a high molecular weight as described above may be obtained through the methanol solution preparing step and the polymerization step described above. For example, in the polymerization step, when the content of the monomer represented by formula (1), which is contained in the polymerization reaction liquid, is set to 20 wt % or more, polyalkoxyalkyl (meth)acrylate having a weight average molecular weight of 200,000 or more may be obtained.

The weight average molecular weight of the polyalkoxyalkyl (meth)acrylate is, for example, more than 300,000, for example, 400,000 or more in terms of the stability of the coat layer. The upper limit of the weight average molecular weight of the polymer is, but not particularly limited to, for example, 1,000,000 or less, for example, less than 1,000,000, for example, 800,000 or less in terms of the fact that the polymer itself is not gelled and insolubilized. The "weight average molecular weight" of polyalkoxyalkyl (meth)acrylate can be calculated by gel permeation chromatography (GPC) in terms of polystyrene as a standard material.

Water absorbed into the polymer material is classified according to its state into free water (water frozen at 0° C. and having a weak interaction with the polymer material or non-freezing water), intermediate water (water frozen at a temperature lower than 0° C. in a temperature rising process and having an intermediate interaction with the polymer material or non-freezing water), or non-freezing water (water not frozen even at −100° C. due to a strong interaction with the polymer material). For example, in a polymer material having a hydrated structure in which a ratio of intermediate water is high, since the contact of the hydrated structure of biological components such as blood and the non-freezing water is suppressed, the hydrated structure of the biological components is stably maintained. Therefore, the polymer material becomes more excellent in biocompatibility. The polyalkoxyalkyl (meth)acrylate is, for example, one in which a ratio of intermediate water calculated by equation (1) below when equilibrium-hydrated exceeds 32%. That is, in an exemplary embodiment of the present disclosure, an antithrombotic coating material is provided, in which a ratio of intermediate water calculated by equation (1) below with respect to the polyalkoxyalkyl (meth)acrylate that is equilibrium-hydrated (hereinafter, the "ratio of intermediate water calculated by equation (1) below when equilibrium-hydrated" is referred to as a "intermediate water ratio"), exceeds 32%.

Ratio (%) of Intermediate Water=$(a/x) \times 100$     [Equation (1)]:

In equation (1), a and x represents an intermediate water content (wt %) and an equilibrium water content (wt %), respectively, in the polyalkoxyalkyl (meth)acrylate that is equilibrium-hydrated. The expression "equilibrium-hydrated" as used in the present disclosure refers to a state where the water content of the polyalkoxyalkyl (meth)acrylate substantially reaches equilibrium in ultrapure water at 25° C., for example, a state of being hydrated until a weight change per hour falls within ±1 wt %.

The intermediate water ratio described above may be determined by the following method. That is, polyalkoxyalkyl (meth)acrylate is weighed to about 0.1 g, and immersed in an excess amount (a weight at least 100 times the weight of the polyalkoxyalkyl (meth)acrylate) of ultrapure water at 25° C. for a week to thereby be equilibrium-hydrated. At this time, it is confirmed that the weight change per hour falls within ±1 wt %. An appropriate amount of an equilibrium-hydrated sample is taken. After excess water on the surface of the sample is absorbed by a low-dust wiper, the sample is put on a glass petri dish that is weighed in advance, and is weighed within 3 minutes ($W_{aq}$ (g)). Separately, an equilibrium-hydrated sample is dried under vacuum at 120° C. for 1 hour, left to cool in a desiccator for 30 minutes, and then, weighed ($W_{dry}$ (g)). From the measured weight, an equilibrium water content (x, wt %) is calculated based on equation (2) below.

$$\text{Equilibrium water content } (x, \text{wt \%}) = \frac{W_{aq}(g) - W_{dry}(g)}{W_{aq}(g)} \times 100 \quad \text{[Equation (2)]}$$

The equilibrium-hydrated sample is analyzed by a differential scanning calorimetry (hereinafter, "DSC") under the following conditions to thereby determine low-temperature crystallization and fusion behavior of water. Then, the water adsorbed onto the polymer material is classified into free water, intermediate water, and non-freezing water, and a rate of each hydrated structure present in the sample is calculated from the equilibrium water content, a low-temperature crystallization heat ($-\Delta H_{cc}$) at −40° C., and a fusion heat ($-\Delta H_m$) at 0° C. Specifically, an intermediate water content (a, wt %), and optionally, a free water content (wt %) and a non-freezing water content (wt %) are determined.

(DSC Measurement Conditions)

Temperature range: −90° C. (maintained for 10 minutes)→ 50° C.

Temperature elevation rate: 2.5° C./min

Measurement atmosphere: Nitrogen 50 ml/min

Measurement Container hermetic aluminum pan

Apparatus used: DSC Q100 manufactured by TA Instruments (Calculation Method of Weight and Ratio of Each Hydrated Structure)

An equation "Equilibrium water content (wt %)=non-freezing water (wt %)+intermediate water (wt %)+free water (wt %)" is defined, and the weight and ratio of each hydrate structure are calculated by the following method.

Intermediate water: $-\Delta H_{cc}$ (mJ) is divided by 334 J/g of solidification heat of water to obtain a weight (mg) of the intermediate water. In addition, the weight of the intermediate water is divided by an amount of the measurement sample to obtain an intermediate water content (a, wt %).

Free water $-\Delta H_m$ (mJ) is divided by 334 J/g of fusion heat of water to obtain a total weight (mg) of the intermediate water and the free water. The weight of the intermediate water is subtracted from the total weight to obtain a weight (mg) of the free water. In addition, the weight of the free water is divided by a measurement sample amount to obtain a free water content (wt %).

Non-freezing water: The measurement sample amount (mg) is multiplied by the equilibrium water content (x, wt %) to obtain an equilibrium water amount (mg). The weight of the intermediate water and the weight of the free water are subtracted from the equilibrium water amount to obtain a weight (mg) of the non-freezing water. In addition, the weight of the non-freezing water is divided by the measurement sample amount to obtain a non-freezing water content (wt %).

When the polyalkoxyalkyl (meth)acrylate having a high intermediate water ratio as described above is used for the coating material, protein adsorption or thrombus adhesion to the coat layer may be further suppressed. The intermediate water ratio in the polyalkoxyalkyl (meth)acrylate is, for example, 35% or more, for example, 37% or more. The upper limit of the intermediate water ratio is not particularly limited (for example, upper limit: 100%).

The intermediate water ratio of the polyalkoxyalkyl (meth)acrylate may be controlled, for example, by appropriately adjusting the weight average molecular weight. For example, the intermediate water ratio may be increased by increasing the weight average molecular weight. For example, in a case of polymethoxyethyl acrylate (PMEA), the intermediate water ratio may be controlled to a high intermediate water ratio higher than 32% by setting the weight average molecular weight to be higher than 90,000.

The structural unit (A) represented by formula (2) is derived from the monomer represented by formula (1). The polymer according to the disclosure may contain structural units derived from the above-described other monomers that are copolymerizable with the monomer represented by formula (1).

The polymer according to the disclosure may contain 50 to 100 mol % of the structural unit (A) in the whole constituent units (100 mol %), but the polymer can contain 70 to 100 mol % of the structural unit (A), and, for example, is composed of the structural unit (A) (100 mol %). When the ratio of the structural unit (A) is set within the range, the adhesion or the antithrombotic property of the coat layer may be enhanced.

The ratios of the structural unit (A) and structural units derived from other monomers in the polymer according to the disclosure may be arbitrarily adjusted by changing the ratios of the monomers used in the polymerization.

The terminal of the polymer according to the present disclosure is not particularly limited and defined appropriately depending on the kind of the raw material used, and can be a hydrogen atom. When the polymer according to the disclosure is a copolymer, the structure of the copolymer is also not particularly limited, but may be any of a random copolymer, an alternating copolymer, a periodic copolymer, or a block copolymer.

The ratios of the structural unit (A) and structural units derived from other monomers in the obtained copolymer may be confirmed by an NMR method or infrared spectrum analysis. For example, in a case of a copolymer including the structural unit (A) and structural units derived from other monomers, the ratios of the structural unit (A) and structural units derived from other monomers in the copolymer may be analyzed by an integral ratio in $^1$H-NMR measurement. Further, when peaks are overlapped in $^1$H-NMR measurement, the ratios may be determined using $^{13}$C-NMR.

In the antithrombotic coating material according to the embodiment, the polymer according to the disclosure is dissolved in methanol or a mixture of water and methanol. As the medium that dissolves the polymer according to the disclosure, methanol or a mixture of water and methanol is used in terms of the solubility of the polymer. If other mediums are used, it can be difficult to dissolve the polymer according to the disclosure at a desired concentration. When a mixture of water and methanol is used as the medium, the volume ratio of water and methanol is not particularly limited as long as the polymer according to the disclosure can be dissolved at a desired concentration, but the volume ratio (v/v) of water:methanol is, for example, 0.1:99.9 to 99:1 (v/v), for example, 80:20 to 99:1 (v/v), for example, 85:15 to 97:3 (v/v).

The amount of the polymer according to the disclosure contained in the antithrombotic coating material according to the embodiment may be arbitrarily set. For example, the polymer according to the disclosure is contained in an amount of 0.01 to 50 wt %, for example, 0.1 to 50 wt %, for example, 0.2 to 10 wt % based on the whole coating material.

The polymer according to the disclosure may be dissolved in methanol or a mixture of water and methanol by using any suitable method without being particularly limited, for example, by a stirrer, a homogenizer, or an ultrasonication.

[Medical Equipment]

The antithrombotic coating material obtained by the production method according to the disclosure, or the antithrombotic coating material dissolved in methanol or a mixture of water and methanol according to the disclosure is appropriately used in a medical equipment. That is, an embodiment of the disclosure relates to a medical equipment which includes a substrate and a coat layer on a substrate surface including a coating film of the antithrombotic coating material obtained by the production method according to the disclosure, or the antithrombotic coating material dissolved in methanol or a mixture of water and methanol according to the disclosure.

Examples of the medical equipment include an intracorporeal implant type artificial organs or therapeutic device, extracorporeal circulation type of artificial organs, catheter, and a guide wire. Specific examples thereof include implant type medical instruments such as an artificial blood vessel that is inserted into a blood vessel or lumen, an artificial trachea, a stent, artificial skin, and an artificial pericardium; artificial organ systems such as an artificial heart system, an artificial lung system, an artificial cardiopulmonary system, an artificial kidney system, an artificial liver system, and an immune regulation system; catheters inserted or indwelled in a blood vessel such as an indwelling needle, an IVH catheter, a medicinal fluid administrating catheter, a thermodilution catheter, an angiographic catheter, a vasodilation catheter, and a dilator or an introducer; or, a guide wire for these catheters, or a stylet; and various suction catheters including a stomach tube catheter, a nutrition catheter, a tube for intubation feeding (ED), a urinary catheter, a urethral catheter, a balloon catheter, and an endrotracheal suction catheter, or catheters inserted or placed in a biological tissue other than a blood vessel such as drainage catheter. For example, the antithrombotic coating material is appropriately used for an artificial lung system in contact with a large amount of blood, or an artificial cardiopulmonary system. For example, when a coat layer including a coating film of the antithrombotic coating material is formed on a hollow fiber membrane of a hollow fiber membrane external blood perfusion type oxygenator, the thickness of the hollow fiber membrane (membrane thickness; a thickness between the inner surface and the outer surface of the hollow fiber membrane) is, for example, 20 μm to 100 μm.

(Substrate)

The material of the substrate of the medical equipment is not particularly limited, and examples thereof include various polymer materials, for example, polyolefin or modified polyolefin such as polyethylene, polypropylene, and ethylene-α-olefin copolymer, polyamide; polyimide; polyurethane; polyester such as polyethylene terephthalate (PET), polybutylene terephthalate (PBT), polycyclohexane terephthalate, and polyethylene-2,6-naphthalate; polyvinyl chloride; polyvinylidene chloride (PVDC); and fluororesin such as polytetrafluoroethylene (PTFE) and ethylene-tetrafluoroethylene copolymer (ETFE), metal, ceramics, carbon, and a composite material thereof. The polymer materials described above may be one that is subjected to a stretching processing (e.g., ePTFE).

The shape of the substrate is appropriately selected depending on the use of the medical equipment, and may take a shape such as tubular, sheet-like, or rod-like. The form of the substrate is not limited to a molded body formed by using the above-described material alone, but a blended molding, an alloyed molding, or a multilayered molding is also available. The substrate may be mono-layered or laminated. When the substrate is laminated, substrates in respective layers may be the same as or different from each other. When the substrate is swelled with a solvent such that the polymer is firmly immobilized, as the material present at least on the substrate surface, the polymer material is exemplary because it can be satisfactorily swelled by the solvent.

The "substrate surface" as used in the disclosure refers to a substrate surface facing biological tissue or body fluid such as blood. When the coat layer having the polymer is formed on the substrate surface, the antithrombotic property on the substrate surface is enhanced. In the medical equipment, the coat layer having the polymer is formed on the substrate surface facing biological tissue, or body fluid such as blood, but the coat layer may be formed on other surfaces.

In order to enhance the stability of the coat layer to the substrate surface, the substrate may be subjected to a surface treatment before forming the coat layer on the substrate surface. A method for the surface treatment of the substrate includes, for example, a method of irradiating active energy rays (electron beam, ultraviolet rays, X-rays, etc.), a method of utilizing a plasma discharge such as arc discharge, corona discharge, or glow discharge, and a method of applying a high electric field, a method of applying ultrasonic vibrations through polar liquid (e.g., water), and a method of treating with ozone gas.

(Coat Layer)

In the medical equipment, a coat layer including a coating film of the antithrombotic coating material is formed on the substrate surface.

In the formation of the coat layer on the substrate surface, the substrate surface is coated by applying a coating liquid containing the antithrombotic coating material (e.g., the methanol dissolution liquid of the polymer according to the disclosure as described above). The term "coated" is intended to include a form in which the entire surface of the substrate is fully covered by the coat layer, as well as a form in which a part of the surface of the substrate is covered by the coat layer, that is, a form in which the coat layer is attached to a part of the substrate surface.

As a method of applying the coating liquid containing the antithrombotic coating material on the substrate surface, any suitable method may be employed, and examples thereof include, but are not particularly limited to, dip coating, spraying, spin coating, dripping, doctor blade, brushing, roll coater, air knife coating, curtain coating, wire bar coating, and gravure coating.

The thickness of the coating liquid may be appropriately adjusted depending on the use of the medical equipment, and is thinner than, for example, 0.1 μm, but not particularly limited thereto.

By drying the substrate surface on which the coating liquid containing the antithrombotic coating material is applied, the coat layer is formed on the substrate surface. The drying process may be appropriately set in consideration of the glass transition temperature of the substrate, and is, for example, 0.5 to 10 hours at 20 to 80° C. Atmosphere in the drying process is not particularly limited, but the drying process may be performed under an air atmosphere, or an inert gas atmosphere such as nitrogen gas or argon gas.

EXAMPLES

The effects of the disclosure will be described using the following examples and comparative examples. However, the technical scope of the disclosure is not limited to the following examples. Operations were carried out at room temperature (25° C.) unless otherwise stated.

1. Preparation Example

Example 1. Weight Average Molecular Weight of Polymer: 140,000

15 g (0.115 mol) of methoxyethyl acrylate (MEA) was dissolved in 80 g of methanol, and the obtained solution was introduced into a four-necked flask, followed by $N_2$ bubbling at 50° C. for 1 hour to prepare a methanol solution (methanol solution preparing step). Then, to the MEA-dissolved methanol solution was added an initiator solution obtained by dissolving 0.015 g of 2,2'-azobis(4-methoxy-2,4-dimethylvaleronitrile) (V-70, manufactured by Wako Pure Chemical Industries, Ltd., 10-hour half-life temperature: 30° C.) in 5 g of methanol, to thereby prepare a polymerization reaction liquid (the monomer content in the polymerization reaction liquid: 15 wt %). Polymerization was carried out under a nitrogen gas atmosphere at 50° C. for 5 hours while stirring the polymerization reaction liquid. The liquid after polymerization was added dropwise into ethanol to precipitate a polymer, which was then recovered. The weight average molecular weight of the recovered polymer was 140,000.

Example 2. Weight Average Molecular Weight of Polymer: 200,000

15 g (0.115 mol) of methoxyethyl acrylate (MEA) was dissolved in 55 g of methanol, and the obtained solution was introduced into a four-necked flask, followed by $N_2$ bubbling at 50° C. for 1 hour to prepare a methanol solution (methanol solution preparing step). Then, to the MEA-dissolved methanol solution was added an initiator solution obtained by dissolving 0.015 g of 2,2'-azobis(4-methoxy-2,4-dimethylvaleronitrile) (V-70, manufactured by Wako Pure Chemical Industries, Ltd., 10-hour half-life temperature: 30° C.) in 5 g of methanol, to thereby prepare a polymerization reaction liquid (the monomer content in the polymerization reaction liquid: 20 wt %). Polymerization was carried out under a nitrogen gas atmosphere at 50° C. for 5 hours while stirring the polymerization reaction liquid. The liquid after polymerization was added dropwise into ethanol to precipitate a polymer, which was then recovered. The weight average molecular weight of the recovered polymer was 200,000.

Example 3. Weight Average Molecular Weight of Polymer: 250,000

15 g (0.115 mol) of methoxyethyl acrylate (MEA) was dissolved in 40 g of methanol, and the obtained solution was introduced into a four-necked flask, followed by $N_2$ bubbling at 50° C. for 1 hour to prepare a methanol solution (methanol solution preparing step). Then, to the MEA-dissolved methanol solution was added an initiator solution obtained by dissolving 0.015 g of 2,2'-azobis(4-methoxy-2,4-dimethylvaleronitrile) (V-70, manufactured by Wako Pure Chemical Industries, Ltd., 10-hour half-life temperature: 30° C.) in 5 g of methanol, to thereby prepare a polymerization reaction liquid (the monomer content in the polymerization reaction liquid: 25 wt %). Polymerization was carried out under a nitrogen gas atmosphere at 50° C. for 5 hours while stirring the polymerization reaction liquid. The liquid after polymerization was added dropwise into ethanol to precipitate a polymer, which was then recovered. The weight average molecular weight of the recovered polymer was 250,000.

Example 4. Weight Average Molecular Weight of Polymer: 320,000

15 g (0.115 mol) of methoxyethyl acrylate (MEA) was dissolved in 30 g of methanol, and the obtained solution was introduced into a four-necked flask, followed by $N_2$ bubbling at 50° C. for 1 hour to prepare a methanol solution (methanol solution preparing step). Then, to the MEA-dissolved methanol solution was added an initiator solution obtained by dissolving 0.015 g of 2,2'-azobis(4-methoxy-2,4-dimethylvaleronitrile) (V-70, manufactured by Wako Pure Chemical Industries, Ltd., 10-hour half-life temperature: 30° C.) in 5 g of methanol, to thereby prepare a polymerization reaction liquid (the monomer content in the polymerization reaction liquid: 30 wt %). Polymerization was carried out under a nitrogen gas atmosphere at 50° C. for 5 hours while stirring the polymerization reaction liquid. The liquid after polymerization was added dropwise into ethanol to precipitate a polymer, which was then recovered. The weight average molecular weight of the recovered polymer was 320,000.

Example 5. Weight Average Molecular Weight of Polymer: 410,000

15 g (0.115 mol) of methoxyethyl acrylate (MEA) was dissolved in 25 g of methanol, and the obtained solution was introduced into a four-necked flask, followed by $N_2$ bubbling at 50° C. for 1 hour to prepare a methanol solution (methanol solution preparing step). Then, to the MEA-dissolved methanol solution was added an initiator solution obtained by dissolving 0.015 g of 2,2'-azobis(4-methoxy-2,4-dimethylvaleronitrile) (V-70, manufactured by Wako Pure Chemical Industries, Ltd., 10-hour half-life temperature: 30° C.) in 3 g of methanol, to thereby prepare a polymerization reaction liquid (the monomer content in the polymerization reaction liquid: 35 wt %). Polymerization was carried out under a nitrogen gas atmosphere at 50° C. for 5 hours while stirring the polymerization reaction liquid. The liquid after polymerization was added dropwise into ethanol to precipitate a polymer, which was then recovered. The weight average molecular weight of the recovered polymer was 410,000.

Example 6. Weight Average Molecular Weight of Polymer: 420,000

80 g (0.61 mol) of methoxyethyl acrylate (MEA) was dissolved in 115 g of methanol, and the obtained solution was introduced into a four-necked flask, followed by $N_2$ bubbling at 50° C. for 1 hour to prepare a methanol solution (methanol solution preparing step). Then, to the MEA-dissolved methanol solution was added an initiator solution obtained by dissolving 0.08 g of 2,2'-azobis(4-methoxy-2,4-dimethylvaleronitrile) (V-70, manufactured by Wako Pure Chemical Industries, Ltd., 10-hour half-life temperature: 30° C.) in 5 g of methanol, to thereby prepare a polymerization reaction liquid (the monomer content in the polymerization reaction liquid: 40 wt %). Polymerization was carried out under a nitrogen gas atmosphere at 50° C. for 5 hours while stirring the polymerization reaction liquid. The liquid after polymerization was added dropwise into ethanol to precipitate a polymer, which was then recovered. The weight average molecular weight of the recovered polymer was 420,000.

Example 7. Weight Average Molecular Weight of Polymer: 800,000

100 g (0.77 mol) of methoxyethyl acrylate (MEA) was dissolved in 95 g of methanol, and the obtained solution was introduced into a four-necked flask, followed by $N_2$ bubbling at 50° C. for 1 hour to prepare a methanol solution (methanol solution preparing step). Then, to the MEA-dissolved methanol solution was added an initiator solution obtained by dissolving 0.1 g of 2,2'-azobis(4-methoxy-2,4-dimethylvaleronitrile) (V-70, manufactured by Wako Pure Chemical Industries, Ltd., 10-hour half-life temperature: 30° C.) in 5 g of methanol, to thereby prepare a polymerization reaction liquid (the monomer content in the polymerization reaction liquid: 50 wt %). Polymerization was carried out under a nitrogen gas atmosphere at 50° C. for 5 hours while stirring the polymerization reaction liquid. The liquid after polymerization was added dropwise into ethanol to precipitate a polymer, which was then recovered. The weight average molecular weight of the recovered polymer was 800,000.

Comparative Example 1. Weight Average Molecular Weight of Polymer: 60,000

15 g (0.115 mol) of methoxyethyl acrylate (MEA) was dissolved in 80 g of toluene, and the obtained solution was introduced into a four-necked flask, followed by $N_2$ bubbling at 80° C. for 1 hour to prepare a toluene solution. Then, to the MEA-dissolved toluene solution was added an initiator solution obtained by dissolving 0.015 g of dimethyl 2,2'-azobis(2-methylpropionate) (V-601, manufactured by Wako Pure Chemical Industries, Ltd., 10-hour half-life temperature: 66° C.) in 5 g of toluene, to thereby prepare a reaction liquid (the monomer content in the reaction liquid: 15 wt %). Polymerization was carried out under a nitrogen gas atmosphere at 80° C. for 5 hours while stirring the reaction liquid. The liquid after polymerization was added dropwise into n-hexane to precipitate a polymer, which was then recovered. The weight average molecular weight of the recovered polymer was 60,000.

Comparative Example 2. Weight Average Molecular Weight of Polymer: 90,000

15 g (0.115 mol) of methoxyethyl acrylate (MEA) was dissolved in 55 g of toluene, and the obtained solution was introduced into a four-necked flask, followed by $N_2$ bubbling at 80° C. for 1 hour to prepare a toluene solution. Then, to the MEA-dissolved toluene solution was added an initiator solution obtained by dissolving 0.015 g of dimethyl 2,2'-azobis(2-methylpropionate) (V-601, manufactured by Wako Pure Chemical Industries, Ltd., 10-hour half-life temperature: 66° C.) in 5 g of toluene, to thereby prepare a reaction liquid (the monomer content in the reaction liquid: 20 wt %). Polymerization was carried out under a nitrogen gas atmosphere at 80° C. for 5 hours while stirring the reaction liquid. The liquid after polymerization was added dropwise into n-hexane to precipitate a polymer, which was then recovered. The weight average molecular weight of the recovered polymer was 90,000.

Comparative Example 3. Weight Average Molecular Weight of Polymer: 120,000

15 g (0.115 mol) of methoxyethyl acrylate (MEA) was dissolved in 40 g of toluene, and the obtained solution was introduced into a four-necked flask, followed by $N_2$ bubbling at 80° C. for 1 hour to prepare a toluene solution. Then, to the MEA-dissolved toluene solution was added an initiator solution obtained by dissolving 0.015 g of dimethyl 2,2'-azobis(2-methylpropionate) (V-601, manufactured by Wako Pure Chemical Industries, Ltd., 10-hour half-life temperature: 66° C.) in 5 g of toluene, to thereby prepare a reaction liquid (the monomer content in the reaction liquid: 25 wt %). Polymerization was carried out under a nitrogen gas atmosphere at 80° C. for 5 hours while stirring the reaction liquid. The liquid after polymerization was added dropwise into n-hexane to precipitate a polymer, which was then recovered. The weight average molecular weight of the recovered polymer was 120,000.

Comparative Example 4

15 g (0.115 mol) of methoxyethyl acrylate (MEA) was dissolved in 30 g of toluene, and the obtained solution was introduced into a four-necked flask, followed by $N_2$ bubbling at 80° C. for 1 hour to prepare a toluene solution. Then, to the MEA-dissolved toluene solution was added an initiator solution obtained by dissolving 0.015 g of dimethyl 2,2'-azobis(2-methylpropionate) (V-601, manufactured by Wako Pure Chemical Industries, Ltd., 10-hour half-life temperature: 66° C.) in 5 g of toluene, to thereby prepare a reaction liquid (the monomer content in the reaction liquid: 30 wt %). Immediately after the addition of the radical polymerization initiator, rapid elevation of the temperature and viscosity was confirmed, and gelation of the reaction liquid occurred. Thus, heating and stirring were stopped.

Comparative Example 5

15 g (0.115 mol) of methoxyethyl acrylate (MEA) was dissolved in 25 g of toluene, and the obtained solution was introduced into a four-necked flask, followed by $N_2$ bubbling at 80° C. for 1 hour to prepare a toluene solution. Then, to the MEA-dissolved toluene solution was added an initiator solution obtained by dissolving 0.015 g of dimethyl 2,2'-azobis(2-methylpropionate) (V-601, manufactured by Wako Pure Chemical Industries, Ltd., 10-hour half-life temperature: 66° C.) in 3 g of toluene, to thereby prepare a reaction liquid (the monomer content in the reaction liquid: 35 wt %). Immediately after the addition of the radical polymerization initiator, rapid elevation of the temperature and viscosity was confirmed, and gelation of the reaction liquid occurred. Thus, heating and stirring were stopped.

Comparative Example 6. Weight Average Molecular Weight of Polymer: 90,000

15 g (0.115 mol) of methoxyethyl acrylate (MEA) was dissolved in 40 g of toluene, and the obtained solution was introduced into a four-necked flask, followed by $N_2$ bubbling at 50° C. for 1 hour to prepare a toluene solution. Then, to the MEA-dissolved toluene solution was added an initiator solution obtained by dissolving 0.015 g of 2,2'-azobis(4-methoxy-2,4-dimethylvaleronitrile) (V-70, manufactured by Wako Pure Chemical Industries, Ltd., 10-hour half-life temperature: 30° C.) in 5 g of toluene, to thereby prepare a reaction liquid (the monomer content in the reaction liquid: 25 wt %). Polymerization was carried out under a nitrogen gas atmosphere at 50° C. for 5 hours while stirring the reaction liquid. The liquid after polymerization was added dropwise into hexane to precipitate a polymer, which was then recovered. The weight average molecular weight of the recovered polymer was 90,000.

TABLE 1

| | | | Methanol | Toluene | Toluene |
|---|---|---|---|---|---|
| Polymerization Solvent | | | | | |
| Polymerization Temperature | | | 50° C. | 50° C. | 80° C. |
| 10-hour half-life Temperature of Polymerization Initiator | | | 30° C. | 30° C. | 66° C. |
| Content of Polymer | 15 wt % | Ex. 1 Mw. 140,000 | | | Comp. Ex. 1 Mw. 60,000 |
| | 20 wt % | Ex. 2 Mw. 200,000 | | | Comp. Ex. 2 Mw. 90,000 |
| | 25 wt % | Ex. 3 Mw. 250,000 | | Comp. Ex. 6 Mw. 90,000 | Comp. Ex. 3 Mw. 120,000 |
| | 30 wt % | Ex. 4 Mw. 320,000 | | | Comp. Ex. 4 Gelled |
| | 35 wt % | Ex. 5 Mw. 410,000 | | | Comp. Ex. 5 Gelled |
| | 40 wt % | Ex. 6 Mw. 420,000 | | | |
| | 50 wt % | Ex. 7 Mw. 800,000 | | | |

[2. Antithrombotic Test]
(Formation of Coat Layer)

The polymers obtained in Examples 2, 3, and 5, and Comparative Example 2 were each dissolved in methanol to a concentration of 1 wt %. Each of ePTFE-made artificial blood vessels (inner diameter: 5 mm, outer diameter: 7 mm, overall length: 5 cm) was immersed in the methanol solution described above, and allowed to stand for 5 minutes. The artificial blood vessel was taken out from the methanol solution, and dried by heating in an oven set at 60° C. for 3 to 4 hours to thereby form a coat layer.

(Antithrombotic Test)

A soft vinyl chloride tube (inner diameter: 6 mm, overall length: 27 cm) was connected with polycarbonate connectors at its both ends. Furthermore, one of the connectors was connected with one end of each of the artificial blood vessels on which the coat layer was formed as described above. The lumen of the soft vinyl chloride tube was filled with 4.5 ml of human blood having anticoagulability enhanced with heparin (heparin concentration: 0.2 units/ml). Thereafter, the connector side which was not connected with the artificial blood vessel and the end of the artificial blood vessel side which was not connected with the connector, were connected with each other to form a loop. The loop was fixed to a cylindrical rotator, and allowed to circulate blood in the lumen of the loop at room temperature (25° C.) in 14 revolutions/min for 120 minutes. The artificial blood vessel was removed from the loop, the lumen of the artificial blood vessel was washed with a physiological saline solution, and thrombus formed on the lumen surface (blood contact surface) was immobilized (25° C.) with 1 wt % aqueous glutaraldehyde solution. After the immobilization, the artificial blood vessel was washed with water and dried, and the blood contact surface of the artificial blood vessel was observed by an electron microscope to confirm the extent of the thrombus formation. A ratio of the area coated by the thrombus formed was calculated based on the area of the entire observation screen by the electron microscope. The results are shown in Table 2.

TABLE 2

| Polymer used for Formation of Coat | Surface Observation Result After Blood Circulation (Level of Thrombus Formation*) |
|---|---|
| Test Example 1 | Example 2 (Mw. 200,000) | 1 |
| Test Example 2 | Example 3 (Mw. 250,000) | 1 |
| Test Example 3 | Example 5 (Mw. 410,000) | 1 |
| Test Example 4 | Comp. Example 2 (Mw. 90,000) | 3 |
| Test Example 5 | No Coat | 4 |

*4: Coated Area 100% 3: 50% ≤ Coated Area < 100% 2: 20% ≤ Coated Area < 50% 1: Coated Area < 20%

As shown in Table 2, the thrombus formation was suppressed by using the antithrombotic coating material containing a high molecular weight polymer. This indicates that the coat layer formed by the coating film of the antithrombotic coating material is stable.

[3. Blood Circulation Test]

According to the following method, the antithrombotic property was evaluated on a substrate (a porous hollow fiber membrane for gas exchange, made of porous polypropylene; thickness of hollow fiber 25 μm) coated with the polymer having a weight average molecular weight of 410,000, obtained in Example 5. That is, the polymer was dissolved in a mixture of water and methanol (water:methanol=95:5 (v/v)) to a concentration of 0.05 wt %, to thereby obtain a coating material (coat liquid). The coating material was filled in a simulated product form (blood circulation module) from a blood import side, and left to stand for 120 seconds. Thereafter, the coating material was removed from the blood circulation module, and dried by blowing air at room temperature (25° C.) for 240 minutes to thereby form a coat layer. This blood circulation module was incorporated into an extracorporeal circulation circuit, and filled with a dilute human fresh blood (heparin: 0.2 units/ml) obtained by mixing 90 ml of heparin (0.45 units/ml)-added human fresh blood and 110 ml of saline solution. The dilute human fresh blood was circulated in the blood circulation module at room temperature (25° C.) in 500 ml/min. After 60 minutes from the circulation start, blood was sampled from the blood circulation circuit, the platelet count was measured, and a ratio of the platelet count after the circulation to the platelet count before the circulation start (100%) (platelet count maintenance rate) was determined. As a result, the platelet count maintenance rate was 91%.

In the blood circulation module coated with the coating material containing the polymer of Example 5, the platelets were maintained at a high maintenance rate. That is, it was confirmed that reduction in platelet count due to coagulation of platelets originated from activation of the coagulation system and the platelet system, or adhesion to a substrate, was decreased, and the antithrombotic property was excellent.

[4. Cast Film Formability Test]

The polymer (weight average molecular weight=420,000) synthesized in Example 6 was dissolved in methanol such that the concentration of the polymer became 1 wt % (coating material (1)). Separately, the polymer (weight average molecular weight=90,000) synthesized in Comparative Example 2 was dissolved in methanol such that the concentration of the polymer became 1 wt % (coating material (2)). For the coating material (1) and the coating material (2), a cast film was fabricated by the following method, and the formability of the film was evaluated.

A biaxially stretched polypropylene film having a thickness of 50 μm and a size of 10 cm×cm was prepared. Onto the polypropylene film, 0.1 g of a coating material was added dropwise, and dried at room temperature (25° C.) for 5 hours to form a coat layer (cast film) on the polypropylene film. Subsequently, the coat layer (cast film) was stained with an aqueous solution of phenol red, and the shape of the cast film was observed.

The cast film fabricated with the coating material (1) was maintained in a circular shape, and the cast film was stable. In contrast, the cast film fabricated with the coating material (2) was not maintained in a neat film shape. In coating material (1), it was considered that the polymer had a high molecular weight so that mutual entanglement of molecular chains was increased, thereby forming a strong cast film.

[5. Analysis of Hydrated Structure]

The polymers obtained in Example 3, Example 5, Example 7, and Comparative Example 2 were each weighed to about 0.1 g, and immersed in an excess amount (a weight 100 times the weight of the polymer) of ultrapure water at 25° C. for a week to thereby be equilibrium-hydrated. It was confirmed that the weight change per hour fell within ±1 wt %. An appropriate amount of each equilibrium-hydrated sample was taken. After excess water on the surface of the sample was absorbed by a low-dust wiper, the sample was put on a glass petri dish that was weighed in advance, and was weighed within 3 minutes ($W_{aq}$ (g)). Separately, an equilibrium-hydrated sample was dried under vacuum at 120° C. for 1 hour, left to cool in a desiccator for 30 minutes, and then, weighed ($W_{dry}$ (g)). From the measured weight, an equilibrium water content (x, wt %), an intermediate water content (a, wt %), a free water content (wt %), and a non-freezing water content (wt %) were calculated by the method described above.

TABLE 3

| | Weight Average molecular weight | Intermediate water content (wt %) | Free water content (wt %) | Non-freezing Water Content (wt %) | Ratio of Intermediate water (%) |
|---|---|---|---|---|---|
| Example 3 | 250,000 | 3.1 | 2.8 | 3.2 | 34 |
| Example 5 | 410,000 | 3.3 | 1.8 | 3.8 | 37 |
| Example 7 | 800,000 | 3.4 | 0.6 | 3.3 | 47 |
| Comparative Example 2 | 90,000 | 3.0 | 4.5 | 1.8 | 32 |

[6. Protein Adsorption Test]

The polymers of Example 7 and Comparative Example 2 were each dissolved in methanol such that the final concentration reached 1 wt %, to thereby prepare a coating material (3) (Mw=800,000) and a coating material (4) (Mw=90,000). The coating material (3) or the coating material (4) was cast on a biaxially stretched polypropylene film (FOP50, manufactured by Futamura Chemical CO., LTD.; thickness: 50 μm), and then, left to stand for drying at room temperature (25° C.) for 48 hours or more. Thereafter, the protein adsorption test was carried out according to the following procedure. In addition, for comparison, the same test was carried out using a biaxially stretched polypropylene film on which no cast film was formed.

Each film was immersed in a TBS solution containing BSA (bovine serum albumin, manufactured by Sigma Co., Ltd.) at a concentration of 1 wt %, and shaken at room temperature (25° C.) for 1 hour. Thereafter, the film was immersed in a TBS-T diluent, and washed for 5 minutes. Washing was repeated three times. Subsequently, the film was immersed in a solution of 5 wt % of skimmed milk (manufactured by Wako Pure Chemical Industries, Ltd.) in TBS, and shaken at room temperature (25° C.) for 1 hour, followed by blocking. The film was immersed in a TBS-T diluent, and washed for 5 minutes. Washing was repeated three times. Subsequently, the film was immersed in a diluent (antibody concentration: 5 μg/ml) of a primary antibody (rabbit anti-bovine albumin antibody, manufactured by BETHYL laboratories, Inc.), and shaken at room temperature (25° C.) for 2 hours. The film was immersed in a TBS-T diluent, and washed for 5 minutes. Washing was repeated three times. The film was immersed in a diluent (a 100-fold antibody dilution of stock solution) of a gold-labeled secondary antibody (goat anti-rabbit IgG antibody, manufactured by KPL laboratories, Inc.), and shaken at room temperature (25° C.) for 2 hours. The film was immersed in a TBS-T diluent, and washed for 5 minutes. Washing was repeated three times. Thereafter, sensitization of adsorbed gold was carried out by a silver enhancer kit (manufactured by Sigma Co., Ltd.). After platinum deposition on the sensitized surface, observation was made with a scanning electron microscopy (apparatus name: S-3400N, manufactured by Hitachi High-Technologies Corporation, magnification: 5,000 times). The compositions of the TBS and the TBS-T diluent are as follows.

TBS: 24.2 g of Tris (trishydroxymethylaminomethane) and 80 g of NaCl were dissolved in pure water, and the pH was adjusted to 7.6 with HCl. Pure water was added up to a total volume of 1 L (0.2 M Tris).

TBS-T diluent: Tween™ was dissolved in the TBS such that the final concentration reached 0.05 wt %.

Figure 1:
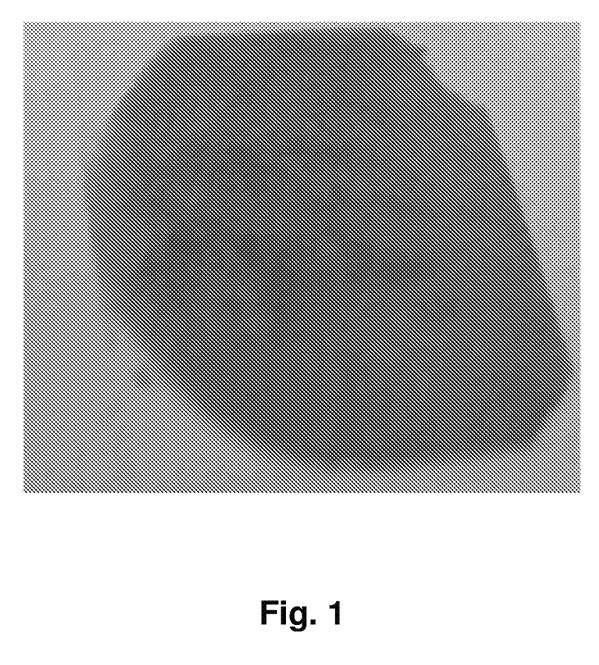
FIG. 1 is a photograph of a cast film of an antithrombotic coating material containing the polymer obtained in Example 6, which is stained with phenol red, according to an exemplary aspect.
Figure 2:
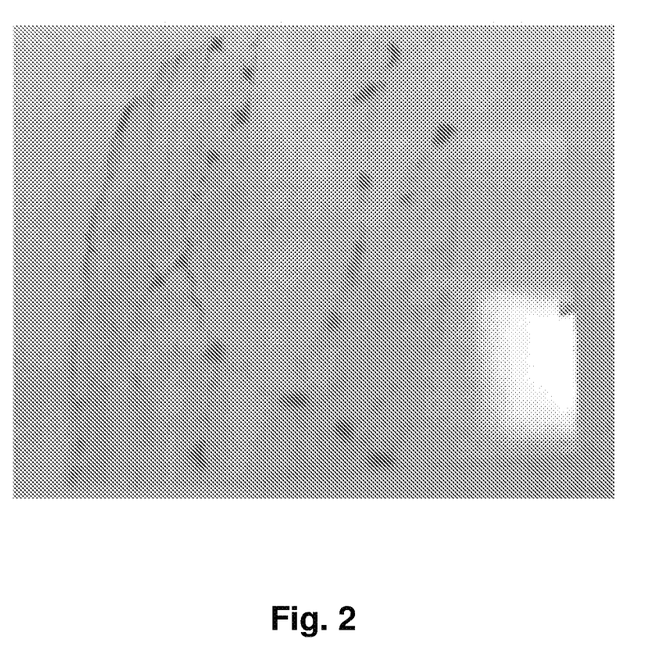
FIG. 2 is a photograph of a cast film of an antithrombotic coating material containing the polymer obtained in Comparative Example 2, which is stained with phenol red.
Figure 3A:
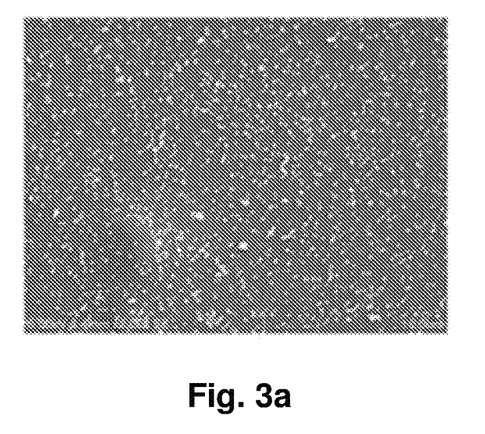
FIG. 3A is a photograph depicting protein adsorption test results for an untreated polypropylene film, according to an exemplary aspect.
Figure 3B:
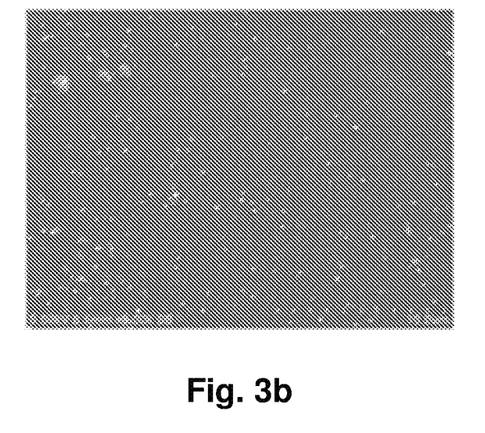
FIG. 3B is a photograph depicting a film formed with a cast film of an antithrombotic coating material containing the polymer obtained in Comparative Example 2.
Figure 3C:
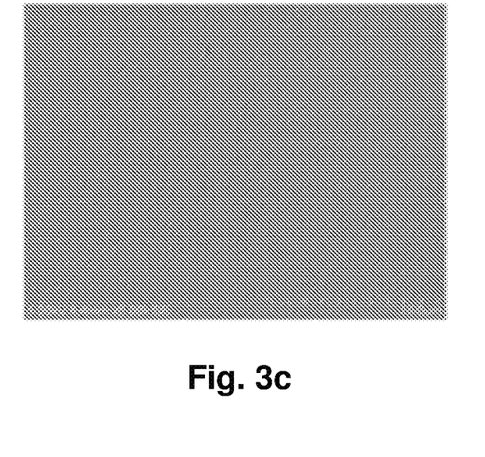
FIG. 3C is a photograph depicting a film formed with a cast film of an antithrombotic coating material containing the polymer obtained in Example 7, according to an exemplary aspect.

The results are illustrated in FIG. 3. As illustrated in FIG. 3, as compared with the cast film having a coat layer formed of a coating material 4 (FIG. 3b), in the cast film having a coat layer formed of a coating material 3 (FIG. 3c), silver particles are substantially not observed, and a protein adsorption amount was very small. It has been found that, in a case of being equilibrium-hydrated, the coating material containing polyalkoxyalkyl (meth)acrylate with a high proportion of intermediate water, has an excellent coatability and a very small protein adsorption amount.

The detailed description above describes exemplary aspects of methods for producing an antithrombotic coating material and antithrombotic coating materials. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An antithrombotic coating material, comprising:
polyalkoxyalkyl (meth)acrylate that contains a structural unit (A) represented by formula (2):

wherein in formula (2), $R^1$ represents a hydrogen atom or a methyl group, $R^2$ represents an alkylene group having 1 to 4 carbon atoms, and $R^3$ represents an alkyl group having 1 to 4 carbon atoms,
wherein the polyalkoxyalkyl (meth)acrylate has a weight average molecular weight of 200,000 or more,
wherein the polyalkoxyalkyl (meth)acrylate is dissolved in methanol or a mixture comprising water and methanol,
wherein the polyalkoxyalkyl (meth)acrylate is not a block copolymer, and
wherein the polyalkoxyalkyl (meth)acrylate is composed of 100 mol % of the structural unit (A).

2. The antithrombotic coating material according to claim 1, wherein a ratio of intermediate water calculated by equation (1) below with respect to the polyalkoxyalkyl (meth)acrylate that is equilibrium-hydrated, exceeds 32%:

Ratio (%) of Intermediate Water=(a/x)×100     Equation (1):

wherein in equation (1), a and x represent an intermediate water content (wt %) and an equilibrium water content (wt %), respectively, in the polyalkoxyalkyl (meth)acrylate that is equilibrium-hydrated.

3. The antithrombotic coating material according to claim 1, wherein the weight average molecular weight of the polyalkoxyalkyl (meth)acrylate is less than 1,000,000.

4. The antithrombotic coating material according to claim 1, wherein the weight average molecular weight of the polyalkoxyalkyl (meth)acrylate is in a range of from 400,000 to 800,000.

5. The antithrombotic coating material according to claim 1, wherein in formula (1), $R^1$ is a hydrogen atom, $R^2$ is a methylene group or an ethylene group, and $R^3$ is a methyl group.

6. The antithrombotic coating material according to claim 1, wherein the polymer is contained in the antithrombotic coating material in an amount of 0.2 to 10 wt % based on the antithrombotic coating material material.

7. The antithrombotic coating material according to claim 1, wherein the polyalkoxyalkyl (meth)acrylate is dissolved in a solvent consisting of methanol or a solvent mixture consisting of water and methanol.

8. A medical device, comprising:
   a substrate comprising a polymer material, and
   the antithrombotic coating material according to claim 1, wherein the antithrombotic coating material is coated on a surface of the substrate.

9. The antithrombotic coating material according to claim 1, wherein the weight average molecular weight of the polyalkoxyalkyl (meth)acrylate is in a range of from 200,000 to 800,000.

10. An antithrombotic coating material, comprising:
    polyalkoxyalkyl (meth)acrylate that contains a structural unit (A) represented by formula (2):

(2)

wherein in formula (2), $R^1$ represents a hydrogen atom or a methyl group, $R^2$ represents an alkylene group having 1 to 4 carbon atoms, and $R^3$ represents an alkyl group having 1 to 4 carbon atoms, wherein the polyalkoxyalkyl (meth)acrylate has a weight average molecular weight in a range of from 200,000 to 800,000, wherein the polyalkoxyalkyl (meth)acrylate is dissolved in methanol or a mixture comprising water and methanol, and wherein the polyalkoxyalkyl (meth)acrylate is composed of 100 mol % of the structural unit (A).

\* \* \* \* \*